United States Patent [19]

Ryan et al.

[11] Patent Number: 5,437,974
[45] Date of Patent: Aug. 1, 1995

[54] DNA SEQUENCE AND ENCODED POLYPEPTIDE USEFUL IN THE DIAGNOSIS OF HEPATITIS DISEASE

[75] Inventors: Terence E. Ryan, Danbury, Conn.; Badr Saeed, Arlington Heights, Ill.; Mark K. Kieselburg, Mansfield, Mass.; Robert E. Byrne, Buffalo Grove; Priscilla W. Stevens, Evanston, both of Ill.; Terukatsu Arima, Kagoshima, Japan; John Todd, LaFayette, Calif.

[73] Assignee: Dade International Inc, Deerfield, Ill.

[21] Appl. No.: 833,838

[22] Filed: Feb. 4, 1992

[51] Int. Cl.$^6$ ............... C07K 14/005; G01N 33/53
[52] U.S. Cl. ........................ 435/5; 530/324; 424/189.1; 436/820; 436/518; 436/526
[58] Field of Search ............ 530/324, 334; 424/89, 424/189.1; 436/820, 518, 526; 435/5

[56] References Cited

U.S. PATENT DOCUMENTS 5,106,726 4/1992 Wang ........................... 435/5

FOREIGN PATENT DOCUMENTS 0363025 6/1989 European Pat. Off. .

OTHER PUBLICATIONS

Merrifield, R. B., Solid Phase Peptide Synthesis. I. The Synthesis of a Tetrapeptide. J. Am. Chem. Soc. 85:2149–2154, 1963.

Hollinger, "Non-A, Non-B Hepatitis Viruses," *Virology* (2nd ed.) 2239–73 (B. N. Fields et al., Eds. Raven Press, N.Y. 1990).

Arima et al., "Cloning of a cDNA associated with acute and chronic hepatitis C infection generated from patients serum RNA," *Gastroenterol. Jpn.* 24:540 (1989).

Arima et al., "A lambda gt11–cDNA clone specific for chronic hepatitis C generated from pooled serum presumably infected by hepatitis C virus," *Gastroenterol. Jpn.* 24:545 (1989).

Arima et al., "Cloning of serum RNA associated with hepatitis C infection suggesting heterogeneity of the agent(s) responsible for the infection," *Gastroenterol. Jpn.* 24:685 (1989).

Arima et al., "A cDNA clone encoding a peptide highly specific for hepatitis C infection," *Gastroenterol. Jpn.* 25:218 (1990).

Primary Examiner—Toni R. Scheiner
Assistant Examiner—Donna C. Wortman
Attorney, Agent, or Firm—Daniel F. Coughlin; Cynthia G. Tymeson

[57] ABSTRACT

A novel cDNA clone, 20E, has been isolated and characterized as encoding a previously unknown polypeptide antigen recognized by antibodies in the serum of certain patients with non-A non-B hepatitis (NANBH). The nucleic acid sequence is not represented in the genome of the Hepatitis C Virus (HCV). Neither is the nucleic acid sequence represented in the human genome. The data suggest that the RNA sequence corresponding to clone 20E is contained within the genome of an external infective agent other than HCV, and therefore may represent an additional etiologic agent or contributing factor to the development of NANBH in human patients. The 20E nucleic acid and corresponding polypeptide and respective variants thereof will be useful in a variety of procedures directed at prevention and diagnosis of NANBH.

4 Claims, 7 Drawing Sheets

Fig. 2A

DNA Sequence of Clone 20E

AATTCCGGGAAGGTAGTGTCAGGTTTTGCGCCCCACGCCACAAAGCCCTCAA
TTAAGGCCCTTCCATCACAGTCCAAAACGCGGGGTGCGTGTTTCGCGGAGTT
CGTTCTGTTTTGCACCGCCGGAATTC
GCAAGACAAAAACGTGGCGGGCCCTTAAG

Fig. 2B

Amino Acid Sequence of Clone 20E

AsnSerGlyLysValIalSerGlyPheAlaProThrHisLysAlaProGlnArg
SerValPheAlaProProGluPhe

| Strip # | Bleed Date | 20E Reactive | HCV C-100 ELISA Reactive |
|---|---|---|---|
| 20E13-1 | 07/19/88 | − | − |
| 20E13-2 | 07/29/88 | − | − |
| 20E13-3 | 08/02/88 | − | − |
| 20E13-4 | 08/05/88 | − | − |
| 20E13-5 | 08/09/88 | − | − |
| 20E13-6 | 08/12/88 | − | − |
| 20E13-7 | 08/16/88 | − | − |
| 20E13-8 | 08/19/88 | − | − |
| 20E13-9 | 08/23/88 | − | − |
| 20E13-10 | 09/28/88 | − | − |
| 20E13-11 | 11/09/88 | + | + |
| 20E13-12 | 11/22/88 | + | + |
| 20E13-13 | 12/06/88 | + | + |
| 20E13-14 | 12/22/88 | + | + |
| 20E13-15 | 01/13/89 | + | + |
| 20E13-16 | 03/17/89 | + | + |
| 20E13-17 | 05/19/89 | + | + |
| 20E13-18a | 06/15/89 | + | + |
| 20E13-18 | 07/18/89 | + | + |
| 20E13-20 | 08/22/89 | + | + |

← GST/20E fusion

| Strip # | Bleed Date | 20E Reactive | HCV C-100 ELISA Reactive |
|---|---|---|---|
| 20E13-21 | 07/28/88 | − | − |
| 20E13-22 | 08/01/88 | − | − |
| 20E13-23 | 08/04/88 | − | − |
| 20E13-24 | 08/15/88 | − | − |
| 20E13-25 | 08/22/88 | − | − |
| 20E13-26 | 08/25/88 | − | − |
| 20E13-27 | 08/29/88 | − | − |
| 20E13-28 | 09/01/88 | − | − |
| 20E13-29 | 09/08/88 | − | − |
| 20E13-30 | 09/28/88 | − | + |
| 20E13-31 | 10/26/88 | + | + |
| 20E13-32 | 11/09/88 | + | + |
| 20E13-33 | 11/22/88 | + | + |
| 20E13-34 | 12/15/88 | + | + |
| 20E13-35 | 12/22/88 | + | + |
| 20E13-36 | 01/13/89 | + | + |
| 20E13-37 | 01/27/89 | + | + |
| 20E13-38 | 02/17/89 | + | + |
| 20E13-39 | 03/17/89 | + | + |
| 20E13-40 | 04/21/89 | + | + |
| 20E7-34 | 05/19/89 | + | + |
| 20E7-35 | 06/15/89 | + | + |

| Strip # | Bleed Date | 20E Reactive | HCV C-100 ELISA Reactive |
|---|---|---|---|
| 20E13-1 | 07/28/88 | − | − |
| 20E13-2 | 08/01/88 | − | − |
| 20E13-3 | 08/04/88 | − | N.D. |
| 20E13-4 | 08/08/88 | − | − |
| 20E13-5 | 08/11/88 | − | − |
| 20E13-6 | 08/15/88 | − | − |
| 20E13-7 | 08/25/88 | + | − |
| 20E13-8 | 08/29/88 | + | − |
| 20E13-9 | 09/14/88 | + | + |
| 20E13-10 | 10/05/88 | + | + |
| 20E13-11 | 10/19/88 | + | + |
| 20E13-12 | 11/16/88 | + | + |
| 20E13-13 | 11/30/88 | + | + |
| 20E13-14 | 01/04/89 | + | + |
| 20E13-15 | 01/25/89 | + | + |
| 20E13-16 | 02/22/89 | + | + |
| 20E13-17 | 03/29/89 | + | + |
| 20E13-18 | 05/03/89 | + | + |
| 20E13-19 | 05/31/89 | + | + |
| 20E13-20 | 06/28/89 | + | + |
| 20E13-21 | 07/26/89 | + | + |

← GST/20E fusion

DNA SEQUENCE AND ENCODED POLYPEPTIDE USEFUL IN THE DIAGNOSIS OF HEPATITIS DISEASE

FIELD OF THE INVENTION

This invention relates to a DNA sequence and encoded polypeptide, wherein the encoded polypeptide represents an antigen specifically recognized by antibodies in certain patients with Non-A Non-B hepatitis. More particularly, the present invention is concerned with a nucleic acid sequence and encoded polypeptide not represented in the genome of the hepatitis C virus. The nucleic acid and encoded polypeptide of the present invention will be useful in a variety of assays for Non-A Non-B hepatitis.

BACKGROUND OF THE INVENTION

The development of specific and sensitive immunodiagnostic assays for Hepatitis A and Hepatitis B viruses led to the identification of several syndromes collectively known as Non-A Non-B hepatitis (NANBH or NANB hepatitis) (reviewed by Hollinger, Non-A Non-B Hepatitis. In: Fields and Knipe, eds. Virology, 2nd Ed. New York; Raven Press, pp. 2239-73, 1990). One syndrome has been clearly associated with transfusions or other percutaneous events, and has been given the name Non-A Non-B Post-Transfusion Hepatitis (NANBPTH). Another syndrome has been epidemiologically associated with fecal-oral contamination, and is known as Enteric Non-A Non-B hepatitis. A third syndrome, for which no infection event has been identified, is classified as sporadic NANBH. The application of techniques in molecular virology has served to identify a new viral agent (Hepatitis C Virus) associated with NANBPTH, Kuo et al., Science 244: 362 (1989), as well as a new viral agent (Hepatitis E Virus) associated with Enteric NANBH, Reyes et al., Science 247: 133 (1990).

Biophysical and biochemical characterization of virus-like particles from concentrated blood products or plasma implicated in the transmission of NANBPTH has been done. These studies have shown the presence of enveloped virus particles of 25-40 nm diameter whose infectivity is eliminated by treatment with organic solvents. Bradley et al., Gastroenterology 88:773 (1985). In addition, non-enveloped virus-like particles with mean diameter of 27 nm have also been observed separately, or in association with the enveloped particles just described. Bradley et al., J. Med. Virol. (1979). Cross-challenge studies can be interpreted to suggest that more than one type of viral agent may be able to cause NANBPTH. Bradley et al., J. Med. Virol. 6: 185 (1980); Hollinger et al., J. Infect. Dis. 142: 400 (1980); Yoshizawa et al., Gastroenterology 81:107 (1981).

Molecular cloning of RNA found in the plasmas of a chimpanzee and humans infected with NANBPTH have shown the presence of a viral genome of about 10 kb, Houghton et al., EPO Application No. 88310922.5 (1988); Houghton et al., EPO Application No. 90302866.0 (1990); Arima and Fukai, EPO Application No. 89309261.9 (1989); Choo et al., Science 244: 359 (1989); Okamoto et al., Japan J. Exp. Med. 60: 167 (1990); Kato et al., Proc. Natl. Acad. Sci. USA 87: 9524 (1990), with an organization similar to that of the enveloped flaviviruses or pestiviruses. Miller and Purcell, Proc. Natl. Acad. Sci. USA 87: 2057 (1990). This new virus type has been named Hepatitis C Virus (HCV), and antibodies to its encoded proteins are eventually found in approximately 60-80% of NANBPTH patients. Alter et al., New Engl. J. Med. 321: 1494 (1989); Esteban et al., New Engl. J. Med. 323: 1107 (1990); Maeno et al., Nucl. Acids Res. 18: 2685 (1990). Infectivity data consistent with Koch's postulates that clearly demonstrate HCV as a cause of NANBPTH have not been developed. However, a correlative argument can be made that many NANBPTH cases are associated with infection by HCV.

Although HCV has been widely accepted as a strong diagnostic marker for NANBPTH, it is still unclear whether other viral agents can cause this syndrome, and what role HCV plays in cases identified as sporadic NANBH. Several researchers, including one of the present inventors (T.A.), have identified cDNA sequences encoding polypeptides reactive with sera from NANBPTH patients that are not represented in the known sequences of HCV and its variants. Arima et al., Gastroenterology Jpn. 24: 540 (1989); Arima et al., Gastroenterology Jpn. 24: 545 (1989); Arima et al., Gastroenterology Jpn. 24: 685 (1989); Arima et al., Gastroenterology Jpn. 25: 218 (1990); Arima and Fukai, EPO Application No. 89309261.9 (1989). These cDNAs apparently are not encoded by the human genome, and therefore are not host-specified responses to the hepatitis disease state. Although their utility in diagnosis has been established, their source and relationship to the disease process remains obscure.

SUMMARY OF THE INVENTION

The applicants prepared nucleic acids from plasma fractions of NANBH patients. These fractions were enriched for virus and virus-like particles by physical and chemical procedures. Extracted nucleic acids were converted into double-stranded complementary DNA (cDNA) and introduced into a derivative of bacteriophage lambda. These lambda phage containing recombinant DNA from NANBH patients were then screened for the production of recombinant-encoded proteins reactive with antibodies contained within the blood of NANBH patients.

One recombinant phage, designated 20E, was found to contain a recombinant DNA insert that encodes a polypeptide sequence that specifically reacts with certain sera obtained from NANB hepatitis patients. This polypeptide antigen detects antibodies present in the blood of several NANB hepatitis patients, and appears to have utility in the detection and screening of this disease. The nucleotide sequence of clone 20E and its encoded polypeptide are unrelated to the virus thought to cause most NANB hepatitis cases, namely HCV. In addition, the nucleotide sequence of clone 20E does not appear to be contained within human chromosomal DNA. This latter result suggests that clone 20E is contained within the genome of an external infective agent associated with NANB hepatitis other than hepatitis C virus, and therefore may represent an additional etiologic agent or contributing factor to the development of NANB hepatitis in human patients.

In other aspects of the present invention, the applicants describe a variety of immunodiagnostic and probe assays for the detection of anti-20E polypeptide antibodies and 20E-related nucleic acids in a patient sample. The 20E polypeptide in question is produced through expression in compatible host cells of recombinant bacteriophage or recombinant plasmid vectors, or through chemical synthesis. Vaccines for protection against the agent represented by clone 20E are formulated as compositions including one or more of the immunodiagnostic epitopes represented in the 20E polypeptide. Moreover, polyclonal and monoclonal antibodies directed against one or more of the immunodiagnostic epitopes of the 20E polypeptide are readily produced using techniques known to those skilled in the art. Such antibodies, or active fragments thereof, are useful as passive immunization agents against the agent represented by clone 20E. Additionally, DNA sequences flanking those described within this invention will have utility in the diagnosis of NANBH and other diseases. These additional sequences can be easily isolated using standard techniques given the sequence of clone 20E.

(A) A membrane lifted from a bacteriological plate containing E. coli infected with wild-type λgt11 clone 20E, and reacted with plasma pooled from patients suffering from NANB hepatitis. Antibody binding to the membrane is detected by a chromogenic enzyme reaction, resulting in a dark spot.

Figure 1B:
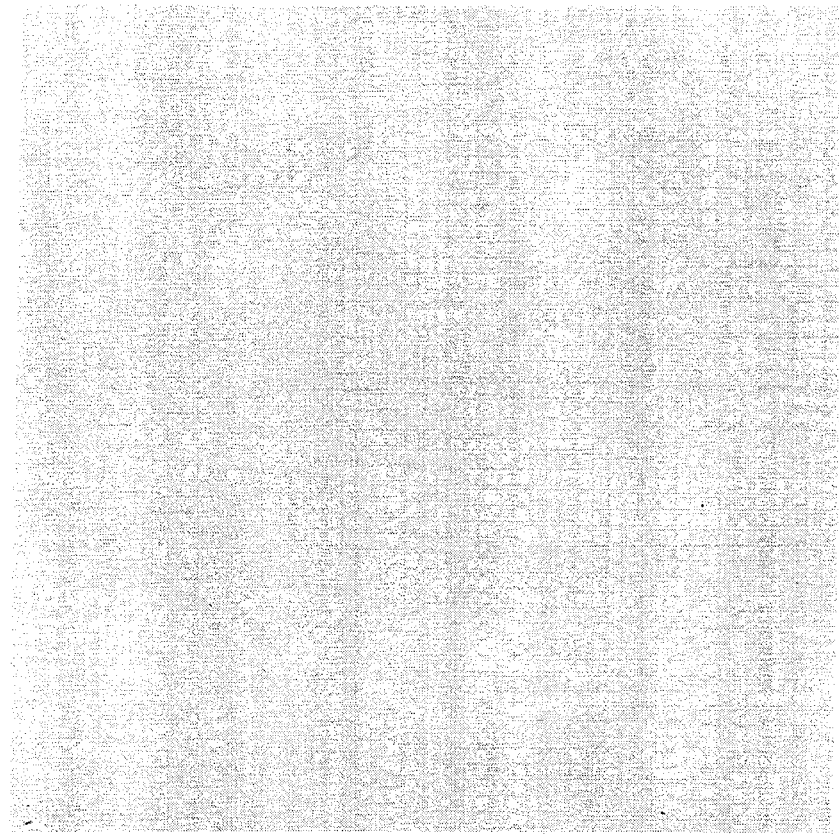
FIG. 1
Figure 1A:
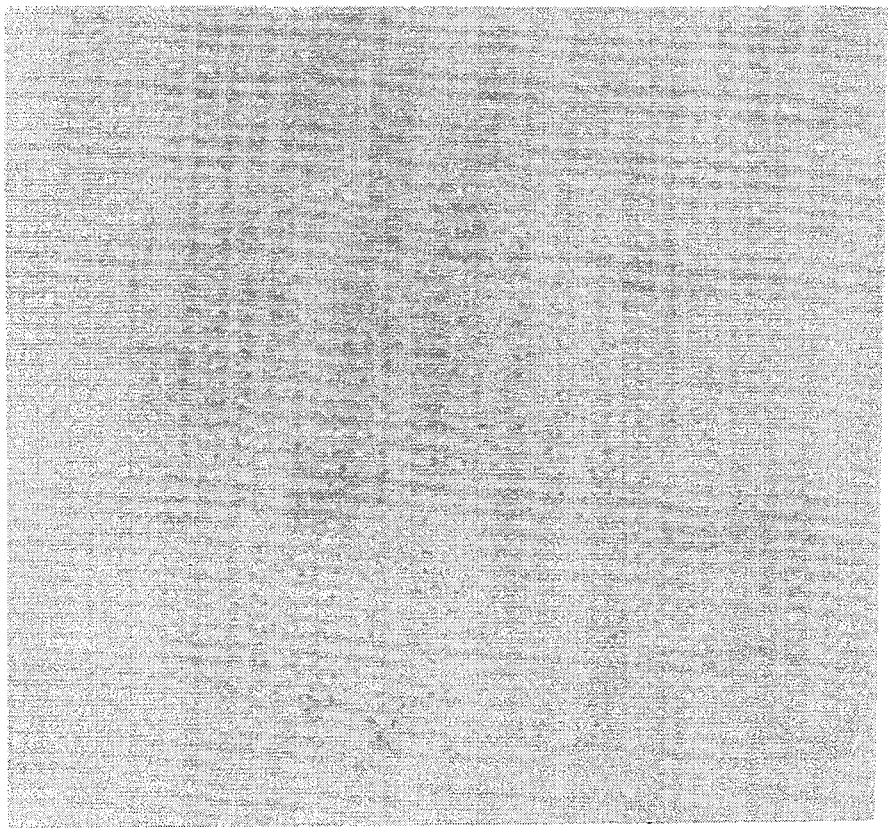

(B) A membrane lifted from a bacteriological plate containing E. coli infected with wild-type λgt11 and reacted with the same plasma as described in FIG. 1(A).

FIG. 2

(A) The DNA sequence of the recombinant insert found in λgt11 phage clone 20E.

(B) The deduced amino acid sequence of the recombinant insert found in λgt11 phage clone 20E.

FIG. 3

(A) A Southern transfer of BamHI-digested human placental DNA probed with a concatenated 450 bp fragment of exon 14 of the human tyrosine hydroxylase gene.

Figure 3A:
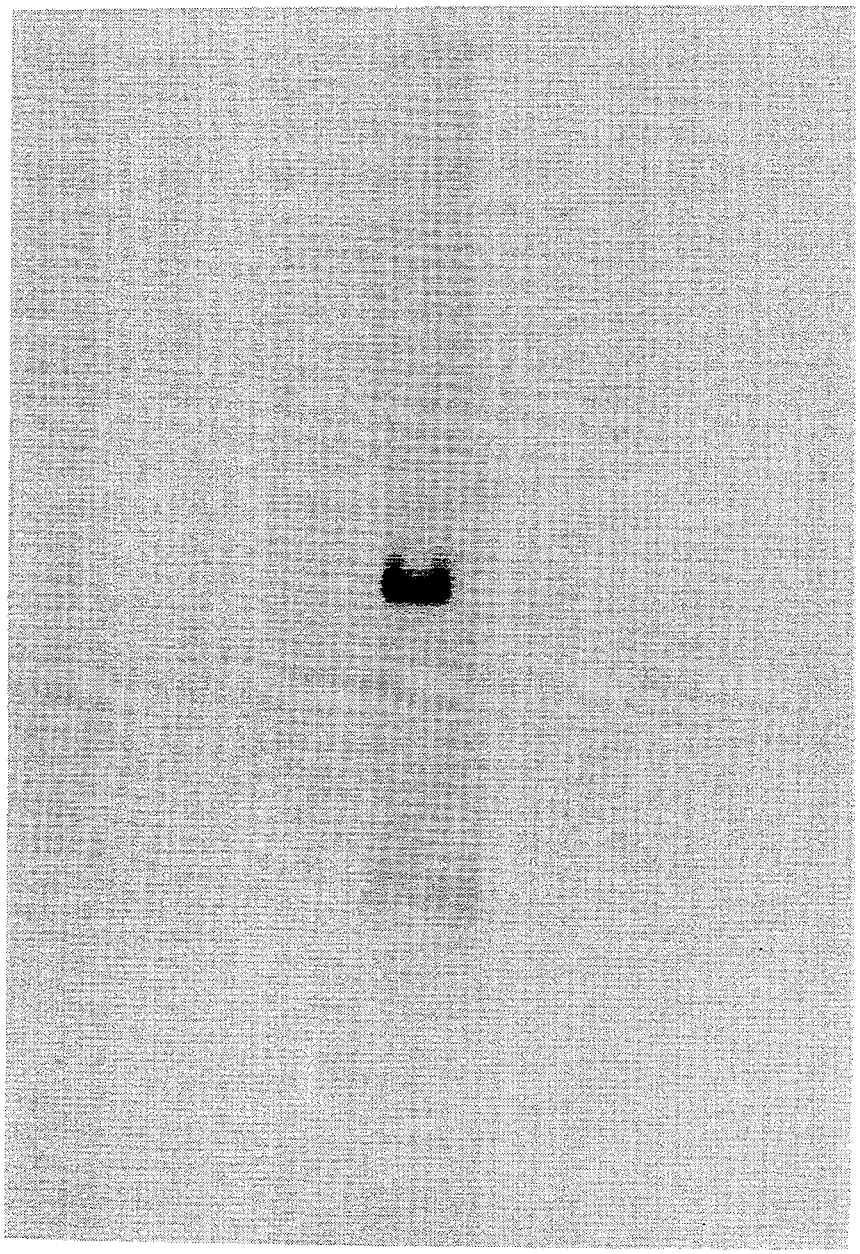

(B) A Southern transfer of Hind III (lane 1), EcoRI (land 2), and BamHI-digested (lane 3) human placental DNA, probed with a concatenated 90 bp fragment representing clone 20E sequence DNA. The DNA in this figure (B) was electrophoresed in the same gel, and transferred to the same membrane as the sample in FIG. 3(A).

FIG. 4

(A) Western blots of purified glutathione-S-transferase/clone 20E protein reacted with serial serum samples from patient 02190D (NANB hepatitis) purchased from Serologicals, Inc. The asterisk represents the bleeding in which anti-HCV antibodies detectable by ELISA (Ortho Diagnostics, Inc.) first become detectable.

(B) Comparison of the Western blot immunoreactivity to purified glutathione-S-transferase/clone 20E protein and anti-HCV ELISA reactivity (Ortho Diagnostics, Inc.) for the above patient.

FIG. 5

(A) Western blots of purified glutathione-S-transferase/clone 20E protein reacted with serial serum samples from patient 20830D (NANB hepatitis) purchased from Serologicals, Inc. The asterisk represents the bleeding in which anti-HCV antibodies detectable by ELISA (Ortho Diagnostics, Inc.) first become detectable.

(B) Comparison of the Western blot immunoreactivity to purified glutathione-S-transferase/clone 20E protein and anti-HCV ELISA reactivity (Ortho Diagnostics, Inc.) for the above patient.

FIG. 6

(A) Western blots of purified glutathione-S-transferase/clone 20E protein reacted with serial serum samples from patient 00269B (NANB hepatitis) purchased from Serologicals, Inc. The asterisk represents the bleeding in which anti-HCV antibodies detectable by ELISA (Ortho Diagnostics, Inc.) first become detectable.

(B) Comparison of the Western blot immunoreactivity to purified glutathione-S-transferase/clone 20E protein and anti-HCV ELISA reactivity (Ortho Diagnostics, Inc.) for the above patient. (N.D.=not done)

DETAILED DESCRIPTION OF THE PREFERRED EMBODIMENT

A polypeptide having diagnostic utility for NANBH and representing a nucleic acid and amino acid sequence having no detectable relationship to any other described NANBH agent would represent a significant advance over the prior art. Such a polypeptide, as well as the corresponding nucleic acid, would be of great value in the ongoing effort to develop a complete preventative and diagnostic regimen for NANBH. The present invention encompasses such a polypeptide and its corresponding nucleic acid sequence.

RNA was isolated from pooled plasma units obtained from patients displaying the clinical picture of NANBH. This pooled plasma was enriched for virus and virus-like particles by centrifugation in the presence of polyethylene glycol and sodium chloride/sodium citrate. RNA was extracted from the resulting pellet and converted to cDNA, and the cDNA cloned into the EcoRI site of the phage expression vector λgt11. The recombinant bacteriophages were amplified by growth in E. coli and the resulting library was immunoscreened for the presence of NANBH antigens by interaction with an antibody preparation derived from plasma of NANBH patients. A positive clone, "20E," was identified and purified by three successive rounds of plaque amplification and immunoscreening.

The nucleotide sequence of the cDNA insert of clone 20E, as well as the deduced amino acid sequence encoded by the insert (hereinafter "20E polypeptide"), are given in FIG. 2. Neither the nucleotide sequence nor the amino acid sequence shows any homology to the nucleotide sequences of HCV reported in the scientific literature or in various patent applications. Neither do the clone 20E DNA or amino acid sequences display any detectable homology with the available sequences of the hepatitis A, B, or D viruses, or any other sequences catalogued in the major data bases. Finally, the nucleotide sequence of clone 20E does not appear to reside in human chromosomal DNA as indicated by absence of hybridization to Southern blots of restricted human genomic DNA.

Thus, clone 20E represents a novel nucleic acid sequence encoding a novel polypeptide having one or more epitopes recognized by antibodies in patients displaying clinical symptoms of NANBH. Lack of detectable hybridization to human genomic DNA suggests that the nucleic acid sequence represented by the cDNA insert of clone 20E represents a portion of the genome of an external infective agent other than HCV. As such, the agent may represent an additional contributing factor to the development of NANBH in humans.

Given the length of the deduced amino acid sequence (26 amino acids) of the 20E polypeptide, it is unlikely that more than one or two NANBH-specific epitopes are represented in the polypeptide. To investigate further the potential immunodiagnostic utility of the epitope or epitopes represented in the 20E polypeptide, the insert was subcloned into an expression plasmid and expressed as a glutathione-S-transferase (GST) fusion protein in *E. coli*. The GST-clone 20E fusion protein was purified and tested for immunoreactivity to serum from additional control and NANBH patients by Western blotting.

For the Western blot procedure, the GST-clone 20E fusion protein was immobilized on a solid support (polyvinylidene difluoride membrane) following electrophoretic size-fractionation in a polyacrylamide gel. The bound protein was then reacted with test serum under conditions allowing binding of any 20E polypeptide-specific (anti-20E) antibodies to the immobilized protein. Binding of anti-20E antibodies was detected with enzyme-labelled signal antibodies. The signal antibodies comprised alkaline phosphatase-conjugated goat anti-human IgG+IgM. Reaction with an appropriate chromogenic substrate for alkaline phosphatase then provided a visual indicator of the presence or absence of anti-20E antibodies in a particular patient test sample. In this immunodiagnostic format, a positive test is indicative of the presence of a patient's anti-20E polypeptide antibody sandwiched between the immobilized GST-clone 20E fusion protein and the signal antibody. In the absence of anti-20E polypeptide antibody (negative test), the antigen-antibody-signal antibody complex does not form and no chromogenic reaction above background is detected.

As demonstrated in the Examples provided below, the epitope or epitopes represented in the 20E polypeptide have marked diagnostic utility for NANBH. Thus, 15.5% of patients with chronic NANBH, and 24.3% of patients with other forms of NANBH (including acute, sporadic and implicated donor NANBH) possessed detectable antibodies reactive with the 20E polypeptide. In contrast, only 1 of 71 (1.4%) of random blood donors possessed such detectable anti-20E antibodies.

To determine the time course of patient seroconversion to anti-20E polypeptide status, the Western blot immunoassay procedure was additionally applied to serum samples representing serial bleedings of three NANBH patients. The three serum panels were also tested for anti-HCV antibodies using a commercially obtained HCV ELISA kit. Each of the serial bleed panels showed seroconversion to anti-20E polypeptide status with conversion dates comparable to conversion to anti-HCV status. Although comparable, the conversion dates for anti-20E polypeptide status and anti-HCV status were not identical in two of the three panels.

These immunoassay results clearly indicate the immunodiagnostic utility of the clone 20E nucleic acid and polypeptide as a specific non-HCV marker for NANB hepatitis disease. Thus, the 20E polypeptide possesses at least one epitope diagnostic for NANBH. On the basis of the results disclosed herein, the immunodiagnostic utility of the NANBH-diagnostic epitope or epitopes of the 20E polypeptide may be defined as detectable non-HCV immunoreactivity with serum from a percentage of individuals at least about ten times greater for NANBH patients than for random blood donors from a general population of donors. The comparable seroconversion parameters for anti-20E and anti-HCV status suggest a possible simultaneous infection of HCV and an infectious agent represented by clone 20E. The serum pool used to construct the phage library from which clone 20E was isolated was entirely human in origin, and was not known to be particularly enriched for NANBH agents. That is, the human serum pool was not necessarily classifiable as a "high-titer" serum pool. In contrast, the library used to originally isolate HCV by expression screening was obtained from high titer serum of an experimentally infected chimpanzee. Choo et al., *Science* 244: 359 (1989). It is possible that clone 20E is derived from an agent that has a host range restricted to humans, or at least exclusive of chimpanzees, which would not have been detected by the strategy used to discover HCV.

The 20E polypeptide will be useful in any immunoassay format utilizing a polypeptide target. In such formats, the 20E polypeptide, fragments of the 20E polypeptide, or 20E polypeptide (or fragments thereof) coupled to another molecule such as a fusion protein, are coated onto a solid matrix such as paramagnetic microparticles. Attachment of the polypeptide to the solid matrix may be by passive or covalent coating methods. Following an incubation step in the presence of anti-20E polypeptide antibodies, the bound antibody-20E polypeptide complex is separated from any unreacted antibodies by magnetic separation. Detection of complexed anti-20E antibody can be carried out by reaction with anti-human antibody antibodies with attached "signal" enzymes such as alkaline phosphatase as described above for the Western blot format. Upon separation of the tagged complex on the paramagnetic particles by magnetic separation and washing, a signal-producing substrate is added. The amount of signal measured is directly proportional to the amount of anti-20E antibody present in the sample.

In a further alternative embodiment, the 20E polypeptide of the present invention may be coated onto microtiter plate wells in the classical enzyme linked immunoabsorbent assay (ELISA), incubated with sample, washed, and an enzyme-conjugated anti-human antiserum added. Glass fiber filters may also be utilized as the solid substrate in a radial partition chromatography format. Detection is conventionally carried out by adding the appropriate substrate/chromogen and measuring the resultant product. For a general discussion of ELISA see Langone et al., Immunological Techniques, Part D Immunoassay. In: *Methods in Enzymology*, p. 84 (1982).

Further alternative assay formats applicable to the polypeptide of the present invention include without limitation Western blot as described above and as referenced in Towbin et al., *Proc. Natl. Acad. Sci*, 76: 4350 (1979); radio-immunoassay, Walsh et al., *J. Infect. Dis.* 21: 550 (1970); competitive assays, Diamandis, *Clin. Biochem.* 21: 139 (1988); noncompetitive assays, Crook et al., *J. Gen. Virol.* 46: 29 (1980); immunoprecipitation, Tojo et al., *Clin. Chem.* 34: 2423 (1988); dot blots, Jahn et al., *Proc. Natl. Acad. Sci. USA* 81: 1684 (1984); and PCFIA, Jolley et al., *J. Immunol. Meth.* 67: 21 (1984).

The 20E polypeptide and fragments thereof also have potential utility as vaccines for the prevention, amelioration or treatment of NANBH. As documented in Examples 4 and 5 below, the epitope or epitopes represented by the 20E polypeptide have been shown to react with antibodies present in the serum of certain NANBH patients. It is therefor likely that the 20E polypeptide or fragments thereof, coupled, if necessary, to appropriate carrier macromolecules [see, e.g. Golub, E. S., *Immunology: A Synthesis*, (1987)], will generate a NANBH-specific immune response in humans immunized with such polypeptides. The 20E polypeptide or appropriate fragments may be expressed from recombinant vectors or produced by chemical synthesis, as isolated polypeptide or as a component of a fusion protein. The polypeptide or fusion protein may be administered to humans in a pharmaceutically acceptable carrier known to those skilled in the art (see, e.g., Golub, supra) in order to elicit an immune response directed against the etiologic agent represented by the 20E polypeptide.

The 20E polypeptide also may be used to generate, using known procedures, materials that could function as components of passive immunization therapies. For example, the 20E polypeptide or fragments thereof may be employed to generate polyclonal or monoclonal antibodies directed against the agent represented by the 20E polypeptide. Such antibodies, or immunoreactive portions thereof, can be used to impart immunity to the 20E agent by direct injection in a pharmaceutically acceptable carrier into a patient's bloodstream. The rationale for passive immunization is that the injected antibodies, independently of the patient's endogenous immune system, bind to and facilitate inactivation and removal of the disease-causing agent. Passive immunization has been found effective in conferring at least transient immunity to a wide array of disease agents. For example, passive immunization with monoclonal antibodies has conferred resistance to several of the flaviviruses. Schlesinger et al., *Technological Advances in Vaccine Development* (L. Laskey, ed.), pages 11–20 (1988). Similarly, passive immunization with polyclonal antibodies has conferred resistance to simian immunodeficiency virus and human immunodeficiency virus type 2. Putkonen et al., *Nature* 352: 436 (1991).

Methods for producing polyclonal and monoclonal antibodies with polypeptide starting materials are well established in the scientific literature. For example, the immunoglobulin fraction of a subject immunized with 20E polypeptide could be affinity purified on a column containing 20E polypeptide bound to a solid phase. This would provide a purified preparation of polyclonal antibodies directed against the 20E polypeptide. Likewise the 20E polypeptide could be used to generate hybridoma cell lines secreting monoclonal antibodies directed against the 20E polypeptide. Such hybridomas can be generated, and the secreted monoclonal antibodies isolated and purified, using well-known methods as described, for example, in Kohler, *Science* 233: 1281 (1986).

The disclosed nucleic acid sequence of clone 20E also will be useful in a variety of assay formats utilizing nucleic acid targets. The clone 20E nucleic acid sequence, for example, may be used as a probe to detect the presence of clone 20E-related nucleic acids in patient serum or tissues. The clone 20E sequence, or a fragment thereof, is labelled with an appropriate radioactive tag (e.g., $^{32}P$) or with an appropriate non-radioactive tag (e.g., biotin) and hybridized to either amplified or unamplified nucleic acid from patient serum or body tissue. For amplification of nucleic acid in patient serum or body tissue, any of the amplification systems known to those skilled in the art may be employed. For example, primers based on the disclosed clone 20E sequence may be synthesized and used in the polymerase chain reaction (PCR) to amplify DNA (or cDNA derived from RNA) extracted from serum or tissue. The various steps in performing PCR are described in Mullis et al., U.S. Pat. Nos. 4,683,202 and 4,683,195. Alternatively, self-sustained sequence replication (3SR) as described in Guatelli et al., *Proc. Natl. Acad. Sci. USA* 87: 1874 (1990) may be employed to amplify an RNA target sequence in serum or tissue. In 3SR, an RNA sequence is amplified by first synthesizing a homologous cDNA containing a phage promoter. Following digestion of the RNA strand of the RNA-cDNA duplex (due to presence of an RNAase H activity in the reaction mix) and synthesis of a second DNA strand off the first cDNA to form a DNA duplex, the DNA duplex is transcribed using a DNA-dependent RNA polymerase. The transcripts are then used as substrates for synthesis of more such cDNA's followed by transcription and additional repetitions of the above-described steps. Another RNA-generating amplification method is known as transcription-based amplification system (TAS), first disclosed by Gingeras et al. in WO 880617 and also disclosed in WO 880729. Unlike 3SR, TAS requires strand separation by denaturation since there is no exogenous RNAase H activity present to digest the RNA strand of the RNA-DNA duplex. TAS superficially resembles PCR in that successive rounds of cDNA synthesis require alternating rounds of denaturation.

Hybridization to amplified or unamplified nucleic acid can be accomplished in situ (e.g., on histological tissue sections) or with extracted nucleic acids, and detected with liquid scintillation counting, autoradiography, or appropriate techniques for detecting non-radioactive tags. For a review of nucleic acid hybridization techniques, see Sambrook et al., *Molecular Cloning: A Laboratory Manual* (2nd Ed.) Cold Spring Harbor Laboratory Press, Cold Spring Harbor, N.Y. (1989). It is to be understood that an RNA sequence corresponding to the sequence disclosed in FIG. 2A may be manufactured with procedures available to those skilled in the art and used as an RNA probe in appropriate circumstances.

The entire clone 20E sequence, or any appropriately diagnostic fragment thereof capable of forming a detectable hybrid with a target nucleic acid, may be used for nucleic acid hybridization as described above. Likewise, it is to be understood that the clone 20E sequence readily may be altered with standard site-specific mutagenesis procedures or other techniques (see Sambrook et al., supra) so as to provide an array of probes useful in detecting clone 20E-related NANBH agents that have undergone mutational variation. It is known, for example, that many RNA viruses are hypervariable, and it may be necessary to use known methods as referenced above to provide clone 20E-related sequences adapted for optimum detection of such variants. Generally any nucleic acid sequence capable of hybridizing to the dislcosed clone 20E sequence under low-to-moderate stringency washing conditions (that is, under combinations of temperature and salt concentration approximately 20° C.–30° C. below the calculated melting temperature Tm of a perfectly matched 20E—20E hybrid; see Maniatis et al., *Molecular Cloning: A Laboratory Manual* Cold Spring Harbor Laboratory Press, Cold Spring Harbor, N.Y. (1982); Sambrook et al., supra) will have potential utility as a diagnostic probe for the agent represented by clone 20E.

In like manner, the disclosed clone 20E nucleic acid sequence may be altered at various codon third positions in accordance with the degeneracy of the genetic code without altering the encoded amino acid sequence. On the other hand, it is to be emphasized that minor changes in amino acid sequence (e.g., subsititutions, additions or deletions) may not appreciably affect assay performance because the epitope or epitopes represented by the disclosed 20E polypeptide are not changed to a degree that destroys the immunodiagnostic utility of such an altered polypeptide in an assay for the 20E agent. As such, polypeptides and corresponding epitopes having such minor changes in structure are considered to be substantially similar to, or equivalents of, polypeptides and epitopes having strict homology to the polypeptide and epitope(s) encoded by the disclosed clone 20E nucleic acid sequence.

Additional nucleic acid sequences representing genomic sequences flanking the genomic sequence corresponding to the disclosed clone 20E nucleic acid sequence are readily obtained using standard procedures. Such sequences, whether 5′ or 3′ to the 20E sequence, may enhance the diagnostic utility of the disclosed clone 20E nucleic acid sequence or may have separate utility as nucleic acid probes. In addition, such sequences may encode amino acid sequence enhancing the diagnostic utility of the disclosed 20E polypeptide, or may encode additional NANBH epitopes having independent immunodiagnostic utility. Methods for identifying and isolating such flanking nucleic acid sequences (chromosome "crawling" or "walking") are well known to those skilled in the art. For reviews of various procedures for isolating flanking sequences, see Sambrook et al., supra. For example, the λgt11 library referenced above and described in the Examples provided below may be rescreened with oligonucleotide probes specific for the 5′ or 3′ end portions of the disclosed clone 20E sequence. As such, clones overlapping with the originally isolated clone 20E may be isolated and will contain nucleic acid sequences flanking the disclosed clone 20E sequence. Alternatively, oligonucleotides based on the disclosed clone 20E sequence may be used as primers to generate new cDNA libraries from which additional flanking clones may be isolated.

The dislosed 20E nucleic acid sequence has been cloned in both phage and plasmid vectors as descried in the Examples below. The 20E polypeptide may be expressed from such vectors in *E. coli* (e.g., other prokaryotic hosts, yeast and other eukaryotic hosts such as mammalian cells) also available to those skilled in the art (Sambrook et al., supra).

The vectors usable for subcloning and/or expression of clone 20E or related sequences include any vectors into which a DNA sequence such as represented by clone 20E can be inserted along with any other elements necessary for optimum transcription and translation of the insert sequence. Such vectors can be transferred into and replicated within one or more of the host cell types listed above. It is preferred that the vectors useful in the present invention possess some or all of the following characteristics: (1) be stably maintainable in the host cells for extended periods; (2) be propagated at high copy number in the desired host cell; (3) posses sequence capable of promoting transcription of the insert; (4) possess sequence coding for a selectable trait such as drug resistance; and (5) possess sequence capable of terminating transcription. For expression, preferably the vectors include at least one promoter, at least one Shine-Delgarno sequence [ribosome binding site; Shine and Delgarno, *Nature* 254: 34 (1975)] or like sequence and initiator codon, at least one terminator codon, and at least one sequence encoding a secretory leader or signal sequence. Any other elements necessary for transcription and/or translation of clone 20E-related sequences may be added to the vectors using methods described in the available scientific literature. The general approaches and numerous examples for cloning and expression of insert sequences in vectors adapted for eukayotic and prokaryotic hosts is provided in Sambrook et al., supra, chapters 1–4, 8, 9, 16, and 17. Yeast vectors may include the yeast artificial chromosome vectors as described, for example, in Burke et al., *Science* 236: 806 (1987).

The disclosed clone 20E nucleic acid sequence displays none of the classical consensus glycosylation sites. This indicates that 20E polypeptides expressed from eukaryotic and other host cells should possess the functional epitope characteristics of the disclosed 20E polypeptide. Thus, unpredictability as to appropriate host cells as may be encountered with various proteins requiring specific glycosylation patterns should not be a factor with 20E polypeptide sequences and related sequences.

In alternative embodiments, both the clone 20E nucleic acid sequence and fragments thereof, as well as the 20E polypeptide and fragments thereof, may be chemically synthesized using well-known procedures. For reviews on chemical synthesis of nucleic acids, see Narang, *Tetrahedron* 39: 3 (1983) and Itakura et al., *Ann. Rev. Biochem.* 53: 323 (1984). Polypeptides of desired sequence may be chemically synthesized on commercially available automated peptide synthesizers such as the Milligen-Biosearch Model 9600 Peptide Synthesizers.

The present invention will now be described in detail with reference to the following Examples, which should not be construed to be limiting the scope of the present invention.

EXAMPLE 1

Isolation and DNA Characterization of Clone 20E

During immunoscreening of a cDNA library prepared from pooled plasma of NANBPTH patients, a phage clone (20E) reactive with sera from NANBPTH patients was identified by use of the following method:

Step 1: Plasma units from individuals presenting a clinical picture of NANB hepatitis were clarified to remove fibrin by low-speed centrifugation and subsequently pooled. Polyethylene glycol 4000 (PEG) was added to the clarified plasma at a concentration of 40 grams/liter, and dissolved by stirring on ice for 30 minutes. The suspension was centrifuged at 7000×g for 20 minutes at 4° C. and the pellet resuspended in 10–30 ml of 0.5% NaCl containing 0.5% sodium citrate. The resuspended pellet was incubated for two hours at 4° C., and then centrifuged at 3600×g for 20 minutes at 4° C. The resulting pellet was then extracted for RNA.

Step 2: RNA from PEG/NaCl pellets was extracted by guanidinium isothiocynate, followed by phenol:-chloroform as described by Chomczynski and Sacchi, *Anal. Biochem.* 162:156 (1987). Viral nucleic acids were precipitated several times with isopropanol and ethanol. Conversion to cDNA was accomplished by denaturation with methylmercury hydroxide followed by reverse transcription using a commerical kit (C-clone II, Clontech). Double stranded cDNAs were treated with S1-nuclease and EcoRI methylase, and were blunt-ended by T4 DNA polymerase. After attachment of EcoRI linkers, the cDNAs were ligated into λgt11 arms (Stratagene) and packaged into phage heads (Gigapack II Gold; Stratagene). The resulting phage library represented approximately 10 million clones, of which approximately 66% contained inserts.

Step 3: A 100 ml culture of *E. coli* strain Y1090R- was grown to an optical density of 0.5 at 600 nm wavelength in medium composed of LB broth containing 50 ug/ml ampicillin, 0.2% w/v maltose and 10 mM $MgSO_4$. Bacteria were then pelleted by centrifugation, and resuspended in 9.2 ml of ice-cold 10 mM $MgSO_4$.

Bacteriophage suspensions representing 50,000 plaque-forming units in 300 ul each of SM buffer (50 mM Tris-HCl pH 7.4, 100 mM NaCl, 10 mM $MgSO_4$, w/v gelatin) were mixed with 450 ul each of the bacterial suspension prepared above, and were agitated at 150 rpm for 15 minutes at 37° C. Tubes were then warmed to 47° C., and 9 ml of top agarose (0.75% w/v in LB broth containing ampicillin at 50 ug/ml) was added to each tube of bacteria with phage. These tubes were then poured onto the surface of 150 mm diameter plates of LB agar containing ampicillin (50 ug/ml), allowed to harden, and incubated in an inverted position at 42° C. After approximately three hours of incubation, phage plaques became visible. The plates were then covered with 137 mm diameter nitrocellulose filters that had been previously soaked in a solution of 10 mM isopropylthio-$\beta$-galactoside (BRL) and allowed to dry. The plates were incubated for a further three hours at 37° C., and the membrane orientation marked by piercing the membrane and bacteriological medium several times with an ink-covered needle. Membranes were then removed from the plates, washed with distilled water, and set aside to dry. Dry filters were then incubated in a solution of 2% w/v non-fat dry milk in 1× TBS (0.1M Tris pH 7.4, 0.5M NaCl, 0.1% w/v $NaN_3$) for 15 to 60 minutes at room temperature.

Step 4: Plasmas (10 ml each) from three individuals suspected to have suffered from NANB hepatitis were pooled, and preadsorbed to a bacterial lysate as follows: *E. coli* Y1090R- lysate was prepared by three rounds of homogenization of the bacterial cell pellet (derived from a 4 liter culture) in an APV Gaulin press at 8000 psi. Lysate protein (120 mg) was coupled to 10 ml of washed, activated Sepharose-4B (Pharmacia) according to the manufacturer's instructions. The coupled lysate was divided into two equal portions. The first was treated with 5 ml of 0.1% SDS for 10 minutes, followed by three washes of 30 ml each of 1× TBS (Column A). Column B consisted of the remaining coupled lysate without the SDS treatment. The pooled plasmas for immunoscreening were added to 12 ml of soluble *E. coli* Y1099R- lysate (30 mg/ml protein) in 1× TBS containing 10 mM EDTA and 2 mM phenylmethylsulfonyl fluoride (BRL). The mixture was rocked for 1 hour at room temperature, and then centrifuged at 7100×g for 10 minutes. The supernatant was passed through column A described supra, and the eluate passed twice through column B described supra. The final eluate (about 45 ml) was then incubated with an additional 112 ml of soluble *E. coli* lysate (30 mg protein/ml) for 30 minutes at room temperature. The mixture was centrifuged at 7100×g for 10 minutes, and 40 ml of supernatant (equivalent to 10 ml of untreated pooled plasma) was diluted with 960 ml of 2% w/v non-fat dry milk in 1× TBS.

Step 5: Membranes from Step 3 were aspirated to remove the milk/TBS solution, and 20 ml of treated antibody from Step 4 was added to each filter. Membranes were incubated with the antibody solution overnight at room temperature with gentle rocking. Antibody solution was then removed by aspiration, and membranes washed for 30 minutes with 6 changes of TBS/Tween solution. Alkaline phosphatase-conjugated goat anti-human IgG/IgM (Jackson Immunoresearch) was diluted 1:3500 in 1×TBS containing 2% non-fat dry milk. Membranes were incubated in 20 ml each of this diluted secondary antibody suspension for 2.5 hours at room temperature, and then washed with six changes of 1× TBS/Tween 20. Following the final wash, the membranes were soaked in a solution of 50 mM Tris-HCl pH 9.5 for 10 minutes. Substrate solution (20 ml/membrane of 590 mM Tris-HCl pH 9.5 containing 66 ul of 5-bromo-4-chloro-3-indolylphosphate p-toluidine salt [50 mg/ml in DMF] and 88 ul nitro blue tetrazolium chloride [75 mg/ml in 70% DMF]) was added to the filters, and incubated until reactive plaques had darkened (2-7 minutes). Reactions were terminated by a 5 minute wash in 1% v/v glacial acetic acid solution followed by a water rinse.

Reactive plaques were identified as darkly-staining circles of approximately 1 mm diameter, often exhibiting a "doughnut"-like appearance. One clone, identified as 20E, was found to be reactive to pooled serum from NANBH patients. This bacteriophage plaque was picked by aligning the membrane with the bacteriological plate, and an agarose plug from the plate was removed using the wide end of a Pasteur pipette. Phage in the plug were eluted overnight by incubation at 4°C. in 1 ml of SM buffer containing 50 ul chloroform. The bacteriophage clone was enriched and purified by three successive rounds of immunoscreeing as described supra, this example.

The purified clone and wild-type λgt11 were plated separately at a density of 500 plaque-forming units per plate and reacted with NANBH pooled sera as described supra, this example. The developed immunostaining of these phage plaques is shown in FIG. 1.

EXAMPLE 2

DNA and Encoded Amino Acid Sequence of Clone 20E

To determine the DNA sequence of the recombinant insert contained within phage clone 20E, the following steps were performed:

Step 1: The recombinant DNA insert from phage clone 20E selected by immunoscreening was amplified by PCR using primers LGa: 5'- ACGACTCCT-GGAGCCCGTCAGTA - 3' (SEQ ID NO:1), LG2: 5' - GGTAATGGTAGCGACCGGCGCTC - 3' (SEQ ID NO:2) that flank the EcoRI cloning site of λgt11, cleaved with that enzyme, cloned into plasmid pUC19 and then subcloned into M13mp19 RF DNA for sequencing. The single-stranded DNA (ssDNA) sequence of the insert was determined using the universal primer and modified T7 DNA polymerase according to protocols provided by a commercial kit (Sequenase 2.0, United States Biochemical). Inserts cloned into plasmid vectors for gene expression (see Example 4 infra) were sequenced after denaturation by alkali to determine the orientation of the insert that resulted in 20E immunoreactivity.

The recombinant DNA sequence of clone 20E determined by the above methods, and the deduced amino acid sequence encoded by it, are reproduced in FIG. 2 infra. The sequences display none of the classical N-linked or O-linked glycosylation sites.

Analysis of this DNA and its encoded protein sequence shows no detectable levels of homology with sequences related to HCV reported in the available scientific literature or in various patent applications. Neither do the clone 20E DNA or amino acid sequences display detectable homology with the available sequences of the hepatitis A, B, or D viruses, with the sequences published in the articles and patent application of Arima et al., supra, or with any other sequences entered in the GenBank and EMBL data bases as searched on Oct. 8, 1991.

EXAMPLE 3

Relatedness of Clone 20E to Human DNA

To determine whether the DNA sequence identified as clone 20E was contained within the human genome, direct DNA:DNA hybridizations were performed as follows:

Step 1: Ten microgram amounts of human placental DNA obtained from a commercial vendor (Clontech) were digested with EcoRI, HindIII or Bam HI restriction enzymes. The digested DNA samples were then electrophoresed in a 0.7% agarose gel at 20V. The size-separated DNA fragments were transferred from the gel to an Oncor SURE BLOT membrane using a vacuum blotting system according to the manufacturer's (Pharmacia-LKB) instructions.

Step 2: As a positive control for a single-copy human gene, a fragment of exon 14 of the tyrosine hydroxylase gene was amplified via the polymerase chain reaction technique from 0.5 ug of human placental DNA using the following oligonucleotide primers: (A37G): 5'- AA-TAAGCTTGTGACGGTGATTGGGGCAG-CAGACA - 3' (SEQ ID NO: 3), (T39T): 5' - TAA-GAATTCGAGCTATGCCTCACGCCATC-CAGCGCCCTT - 3' (SEQ ID NO:4).

An amplified band of about 460 base pairs was isolated, then digested with HindIII and EcoRI. The digested DNA was subcloned into HindIII/EcoRI digested pUC19 plasmid, and DNA sequencing confirmed its identity as a portion of the tyrosine hydroxylase gene. The purified tyrosine hydroxylase gene fragment described above was self-ligated to form concatenated DNA by the following method: the gene fragment was liberated from 100 ug of pUC19 plasmid by digestion with HindIII and EcoRI restriction endonucleases, and separated from plasmid DNA by electrophoresis in a 2% agarose gel.

The DNA fragment was eluted from the gel using the method of Vogelstein and Gillespie, *Proc. Natl. Acad. Sci. USA* 76:615 (1979). The eluted DNA was concentrated by ethanol precipitation, quantified by spectrophotometric methods, and a 500 ng amount was ligated to form concatenated gene fragments using T4 DNA ligase and standard methods. Sambrook et al., supra (1989). Similarly, the 20E sequence in pUC19 was excised as an EcoRI fragment and concatenated. These concatenated DNAs were separately labelled by nick-translation using the Klenow fragment of *E. coli* DNA polymerase and $\alpha$-$^{32}$P labelled dATP to generate radioactive probes. Sambrook et al., supra (1989). Concatenation of the gene fragments was necessary to provide a DNA substrate of sufficient size to be a substrate for nick-translation, the preferred method to produce high-specific activity radioactive DNA probes.

Step 3: The membrane containing the digested human DNA was prehybridized and hybridized using the solution (Hybrisol 1) suggested by the membrane distributor (Oncor). DNA probes were added to the appropriate membranes contained within plastic bags to a concentration of $1 \times 10^6$ counts per minute per milliliter of hybridization solution. Blots and probes were incubated with agitation at 45° C. overnight.

Figure 3B:
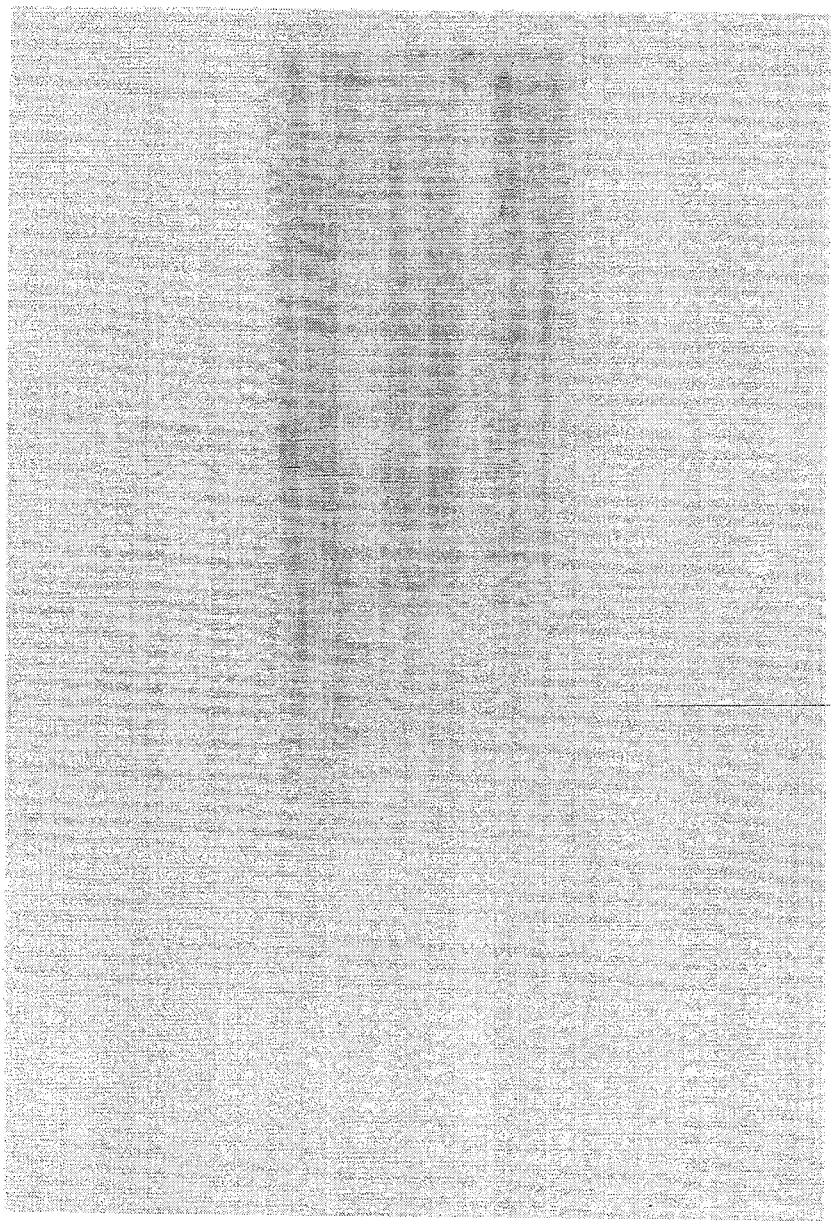

Blots were washed according to the manufacturer's instructions, except that the final wash was performed at 57° C. Dried blots were exposed to Kodak X-omat AR diagnostic film between two DuPont Cronex intensifying screens at $-70°$ C. for 16 hours. The film was developed according to the manufacturer's instructions, and is shown in FIG. 3.

EXAMPLE 4

Reaction of 20E Polypeptide with Control and NANBH Serum

Plasmid pUC19 containing clone 20E insert was digested with EcoRI and the 20E fragment was subcloned into a variant of the plasmid vector pGEX-2T. Smith and Johnson, *Gene* 67:31 (1988). This variant (designated pGEX-2Ta) was constructed by opening the pGEX-2T plasmid by digestion with BamHI restriction endonuclease, filling the overhanging termini by the action of the Klenow fragment of *E. coli* DNA polymerase, and ligating the blunt ends together. Sambrook et al., supra (1989). The peptide encoded by clone 20E was expressed from plasmid pGEX-2Ta as a glutathione-S-transferase (GST) fusion protein in *E. coli* strain DH5α according to methods previously described. Smith and Johnson, supra (1988).

The GST fusion protein was immunoreactive with the serum originally used to isolate the λgt11-clone 20E phage by Western blot test (see below). This result was surprising, in that the modified vector would not be expected to produce in-frame protein expression products from inserted genes isolated from λgt11. Other inserts isolated from λgt11 during the course of this work failed to express as proteins in pGEX-2Ta due to incorrect alignment of the fusion leader with the EcoRI insertion site for these sequences. These results suggest that the clone 20E sequence was unusual, in that its immunogenic expression in λgt11 was due to an abnormal sequence alignment in the original λgt11-clone 20E phage. This abnormal sequence alignment may have been due to the presence of two EcoRI linkers at the 5' end of the molecule, but the exact nature of the sequence alignment has not been determined. The GST-clone 20E fusion protein was purified by the method of Abath and Simpson, *Peptide Res.* 3:167 (1990). Glutathione-S-transferase was similarly purified from bacterial cultures containing unmodified pGEX-2T lacking the 20E insert.

Preparation of pGEX glutathione-S-transferase (GST) 20E Western blot strips was accomplished in two steps by performing sodium dodecyl sulfate (SDS)-polyacrylamide gel (PAGE) using a Laemmli discontinuous buffer system, Laemmli, *Nature* (Lond.) 227:680 (1970). The gel consisted of a 12% separating gel (pH 8.8) and a 4.5% stacking gel (pH 6.8), and was electrophoresed by applying purified GST-20E antigen in 2% SDS, 0.125 M Tris pH 6.8, 10% glycerol, 1% 2-mercaptoethanol and 0.02% pyronin Y tracking dye was boiled for 5 minutes in a water bath. The sample was applied as $2 \times 128$ ul aliquots (2.7 ug each) to two preparative wells (64 mm width each) and electrophoresed at constant current until the tracking dye reached the bottom of the gel.

The apparent molecular weight of GST-20E was estimated by extrapolation from a standard plot of the logarithm of the molecular weight versus the electrophoretic mobility of rainbow molecular weight markers (Amersham Corp., Arlington Heights, Ill.) run in an adjacent 5 mm lane, and was found to be identical to the predicted molecular weight of the fusion protein. The separated proteins were electrotransferred in a tank apparatus (Hoeffer, San Francisco, Calif.) to a polyvinylidene difluoride membrane (Millipore, New Bedford, Mass.) in a Tris-glycine system as described by Towbin et al., *Proc. Natl. Acad. Sci. USA* 76:4350 (1979). After transfer, the membrane was blocked in a solution of 5% powdered non-fat dry milk dissolved in isotonic-buffered saline (IBS; Baxter Scientific Products) as described by Johnson et al., *Gene Anal. Tech.* 1:3 (1984). The membrane was rinsed briefly in IBS, cut into 3 mm×120 mm strips and either used immediately or stored at −20° C. Western blot strips were placed in troughs of an incubation tray (Bio-Rad Laboratories) containing 2 ml each of 5% non-fat dry milk in isotonic buffered saline. Control and test specimens (20 ul) were preincubated for 15 minutes with 100 ug (50 ul–100 ul) of purified pGEX GST lacking the 20E insert to preabsorb GST-reacting antibodies.

The treated specimens were then added directly to each trough and incubated over night at room temperature with gentle agitation. After incubation, the strips were each washed four times for 5 minutes with 5 ml of 0.05 M Tris-3M NaCl) pH 8.0 containing 0.01% NaN$_3$ followed by 2 more 5 ml washes containing IBS only. The strips were then incubated for 2 hours with alkaline phosphatase-conjugated goat anti-human IgG+IgM (Jackson Immunoresearch, Westgrove, Pa.) in IBS 5% non-fat dry milk solution (1:3500). Next, the strips were then washed three times for 5 minutes with 5 ml of IBS 0.3%-Tween-20. The strips from one reaction tray (up to 25 strips) were transferred to a flat-bottom plastic box (19×16 cm) and washed twice for 5 minutes with 0.05 M Tris pH 9.5, 0.05% NaN$_3$ (substrate buffer).

Development of the strips was accomplished with the nitro blue tetrazolium/5-bromo-4-chloro-indolyl phosphate system in substrate buffer as described by Blake et al., *Anal. Biochem.* 136: 175 (1984), and allowed to air dry on blotting paper in the dark. Strongly reactive, weakly reactive and negative controls were run with each group of specimens. Reactivity of clinical specimens was assessed relative to the intensity of a control Western blot developed with one of the sera used in the immunoscreening pool (Example 1). This serum, tested against clone 20E phage plaques, was the weaker of the two reactive sera in the pool. Reactive Western blots were judged to have an equal or greater staining of the 20E-specific band when compared with the control serum. Results of these experiments are given in Table 1, below.

TABLE 1

| Reaction of Clone 20E Fusion Protein with Sera | | |
|---|---|---|
| Population | Reactive | |
| Random Blood Donors | 1/71 | (1.4%) |
| Chronic NANBH | 18/116 | (15.5%) |
| Other NANBH | 9/37 | (24.3%) |

Legend to Table 1: Western blot transfers were incubated with clinical specimens, and scored as reactive or non-reactive to the clone 20E fusion protein band (M.W. ~32,000). The reactivity is expressed relative to a control serum used in all Western blot tests. This serum was a component of the original pooled serum used to discover clone 20E by plaque lift, and represents the weaker of the two pool sera reactive in the plaque-life assay. Reactive samples were judged to be those equal or greater in staining density to the control serum.

Clinical samples from investigators located in the United States, United Kingdom, and Japan were categorized as either chronic NANB disease, or other NANB disease (including acute, sporadic, and implicated donor). Random blood donors were from a United States population.

EXAMPLE 5

Reaction of 20E Polypeptide with NANBH Serial Bleed Panels

Figures 4A, 4B:
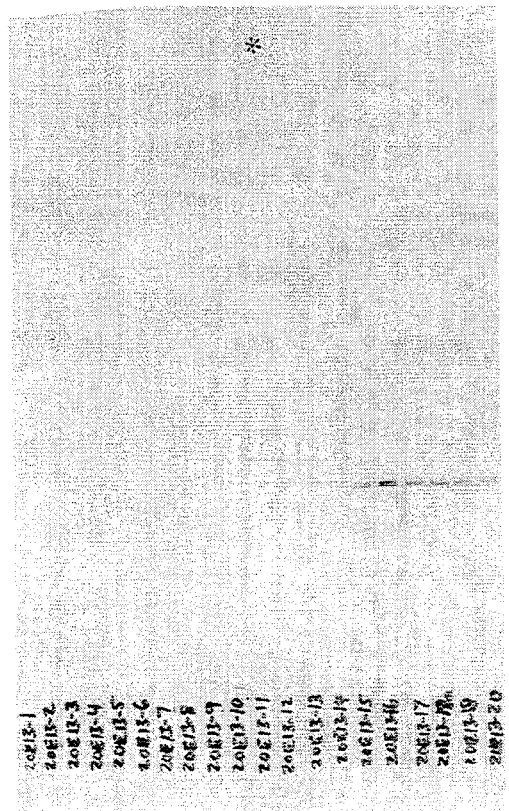
Figures 5A, 5B:
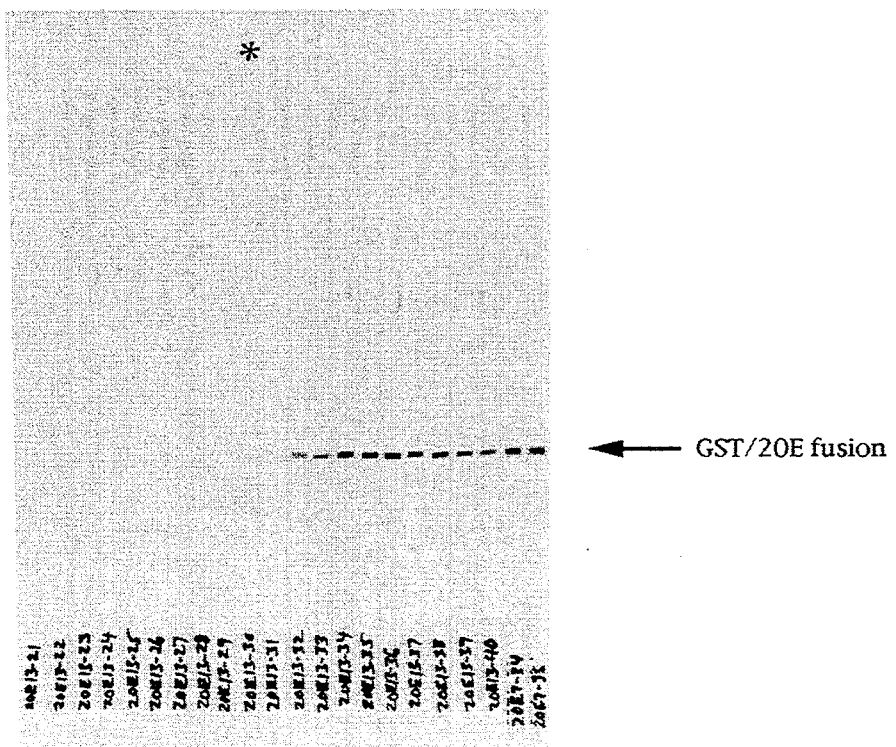
Figures 6A, 6B:
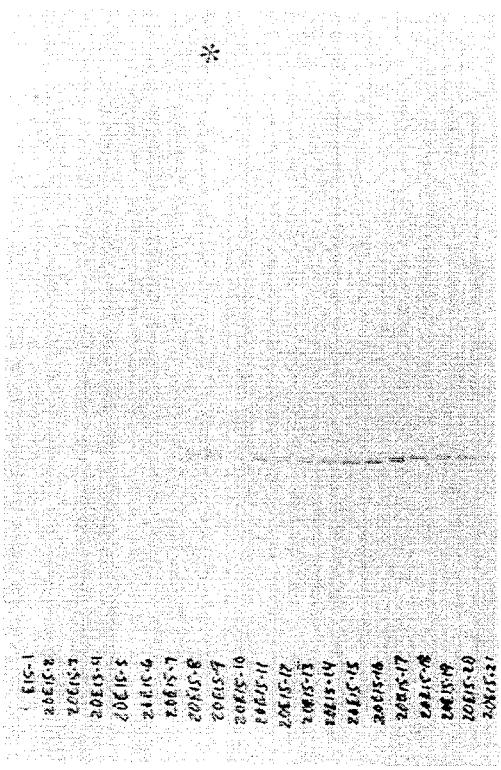

To determine whether NANBH patients seroconvert to anti-20E during or after clinical disease, serum samples representing serial bleedings of 3 NANBH patients were assayed by Western blot to glutathione-S-transferase/clone 20E fusion proteins. These serum samples were processed and assayed as described in Example 4. The serum samples were obtained from a commercial vendor (Serologicals, Inc.), which identified these patients as converting to anti-HCV C-100 protein after NANBH disease as detected by a commercial test (Ortho Diagnostic Systems, Inc.). The three serum panels were tested for anti-HCV antibodies using a commercially obtained HCV ELISA kit. Results of these experiments are provided in FIGS. 4, 5, and 6. Each of the serial bleed panels showed seroconversion to anti-20E polypeptide status with conversion dates comparable to conversion to anti-HCV status. Although comparable, the conversion dates for anti-20E polypeptide status and anti-HCV status were not identical in two of the three panels. That is, in one case, seroconversion to anti-20E status occurred one bleeding period after seroconversion to anti-HCV status (FIG. 5); in the second case, seroconversion to anti-20E status appeared two bleeding periods before seroconversion to anti-HCV status (FIG. 6).

The foregoing detailed description has been provided for a better understanding of the invention only and no unnecessary limitation should be understood therefrom as some modifications will be apparent to those skilled in the art without deviating from the spirit and scope of the appended claims.

What is claimed is:

1. A polypeptide as defined in the Sequence Listing by SEQ ID NO:7.

2. An immunoassay composition, comprising:
(a) a solid substrate; and
(b) the polypeptide of claim 1 coated onto said solid substrate.

3. The composition of claim 2, wherein said solid substrate is a well in a microtiter plate.

4. The composition of claim 2, wherein said solid substrate is a paramagnetic particle.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: Other nucleic acid, synthetic oligonucleotide ( x i ) SEQUENCE DESCRIPTION: SEQ ID NO:1:

ACGACTCCTG GAGCCCGTCA GTA                                        23

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: Other nucleic acid, synthetic oligonucleotide ( x i ) SEQUENCE DESCRIPTION: SEQ ID NO:2:

GGTAATGGTA GCGACCGGCG CTC                                        23

( 2 ) INFORMATION FOR SEQ ID NO:3:

( i ) SEQUENCE CHARACTERISTICS:
        ( A ) LENGTH: 34 base pairs
        ( B ) TYPE: nucleic acid
        ( C ) STRANDEDNESS: unknown
        ( D ) TOPOLOGY: unknown ( i i ) MOLECULE TYPE: Other nucleic acid, synthetic oligonucleotide ( x i ) SEQUENCE DESCRIPTION: SEQ ID NO:3:

AATAAGCTTG TGACGGTGAT TGGGGCAGCA GACA                          34

( 2 ) INFORMATION FOR SEQ ID NO:4:

( i ) SEQUENCE CHARACTERISTICS:
        ( A ) LENGTH: 40 base pairs
        ( B ) TYPE: nucleic acid
        ( C ) STRANDEDNESS: unknown
        ( D ) TOPOLOGY: unknown ( i i ) MOLECULE TYPE: cDNA to genomic RNA ( x i ) SEQUENCE DESCRIPTION: SEQ ID NO:4:

TAAGAATTCG AGCTATGCCT CACGCCATCC AGCGCCCCTT                   40

( 2 ) INFORMATION FOR SEQ ID NO:5:

( i ) SEQUENCE CHARACTERISTICS:
        ( A ) LENGTH: 78 base pairs
        ( B ) TYPE: nucleic acid
        ( C ) STRANDEDNESS: double
        ( D ) TOPOLOGY: unknown ( i i ) MOLECULE TYPE: cDNA to genomic RNA ( x i ) SEQUENCE DESCRIPTION: SEQ ID NO:5:

AATTCCGGGA AGGTAGTGTC AGGTTTTGCG CCCACGCACA AAGCGCCTCA ACGTTCTGTT      60

TTTGCACCGC CGGAATTC                                                          78

( 2 ) INFORMATION FOR SEQ ID NO:6:

( i ) SEQUENCE CHARACTERISTICS:
    ( A ) LENGTH: 78 base pairs
    ( B ) TYPE: nucleic acid
    ( C ) STRANDEDNESS: double
    ( D ) TOPOLOGY: unknown ( i i ) MOLECULE TYPE: cDNA to genomic RNA ( x i ) SEQUENCE DESCRIPTION: SEQ ID NO:6:

```
GAATTCCGGC GGTGCAAAAA CAGAACGTTG AGGCGCTTTG TGCGTGGGCG CAAAACCTGA      60
CACTACCTTC CCGGAATT                                                    78
```

( 2 ) INFORMATION FOR SEQ ID NO:7:

( i ) SEQUENCE CHARACTERISTICS:
        ( A ) LENGTH: 26 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:7:

```
Asn Ser Gly Lys Val Val Ser Gly Phe Ala Pro Thr His Lys Ala Pro
 1               5                  10                 15
Gln Arg Ser Val Phe Ala Pro Pro Glu Phe
                20                  25
```